United States Patent
Roh et al.

(10) Patent No.: US 12,077,723 B2
(45) Date of Patent: Sep. 3, 2024

(54) METHOD OF PREPARING KRILL OIL AND KRILL OIL COMPOSITION

(71) Applicant: DONGWON F&B CO., LTD., Seoul (KR)

(72) Inventors: Jin Chul Roh, Gyeonggi-do (KR); Ju Young Song, Gyeonggi-do (KR); Jun Gu Lim, Gyeonggi-do (KR)

(73) Assignee: DONGWON F&B CO., LTD., Seoul (KR)

( * ) Notice: Subject to any disclaimer, the term of this patent is extended or adjusted under 35 U.S.C. 154(b) by 429 days.

(21) Appl. No.: 17/100,789

(22) Filed: Nov. 20, 2020

(65) Prior Publication Data

US 2022/0041952 A1    Feb. 10, 2022

(30) Foreign Application Priority Data

Aug. 7, 2020  (KR) .................. 10-2020-0099434

(51) Int. Cl.
  *C11B 1/10*      (2006.01)
  *A61K 31/661*    (2006.01)
  *A61K 35/612*    (2015.01)

(52) U.S. Cl.
  CPC .............. *C11B 1/10* (2013.01); *A61K 31/661* (2013.01); *A61K 35/612* (2013.01)

(58) Field of Classification Search
  CPC ........ C11B 1/10; A61K 31/661; A61K 35/612
  See application file for complete search history.

(56) References Cited

U.S. PATENT DOCUMENTS

| | | | |
|---|---|---|---|
| 5,091,117 A | 2/1992 | Athnasios et al. | |
| 2016/0228462 A1 | 8/2016 | Myhren et al. | |
| 2016/0229781 A1* | 8/2016 | Oroskar ................. | C11B 3/008 |
| 2018/0051230 A1* | 2/2018 | Saebo ................. | B01D 61/027 |

FOREIGN PATENT DOCUMENTS

| | | |
|---|---|---|
| CN | 107779258 | 3/2018 |
| CN | 108913352 | 11/2018 |
| CN | 105419936 | 4/2020 |
| JP | S6339991 | 2/1988 |
| JP | 2649416 | 9/1997 |
| KR | 20170118125 | 10/2017 |
| WO | 2012139588 | 10/2012 |
| WO | 2016128830 | 8/2016 |

OTHER PUBLICATIONS

Chunpu et al, Machine Translation (Year: 2019).*
CN109181863A, Machine Translation. (Year: 2019).*
Berezin et al., "Separation of sterols using zeolites," Physical Chemistry Chemical Physics, 2001, vol. 3.
"Antarctic Krill Oil," Mintel, retrieved from the internet: <http://www.gnpd.com>, 2020.
"Extraction, isolation and analysis of phosphatidylcholine from Antarctic krill oil," Aug. 15, 2014, B024-223, China Academic Journal Electronic Publishing House.

* cited by examiner

*Primary Examiner* — Jeffrey S Lundgren
*Assistant Examiner* — Ibrahim D Bori
(74) *Attorney, Agent, or Firm* — Hodgson Russ LLP

(57) ABSTRACT

Disclosed is a method of preparing krill oil. A method of preparing krill oil may include providing a dried krill powder; obtaining an extract after adding spirits of wine to the dried krill powder; obtaining a passing solution from which salt and cholesterol are removed by passing the extract through a column; obtaining a krill concentrate by decompression-concentrating the passing solution; and obtaining krill oil by stationarily positioning a mixture obtained by adding spirits of wine to the krill concentrate, layer-separating the stationarily positioned mixture, extracting a supernatant of the layer-separated mixture, and concentrating the extracted supernatant.

6 Claims, 1 Drawing Sheet

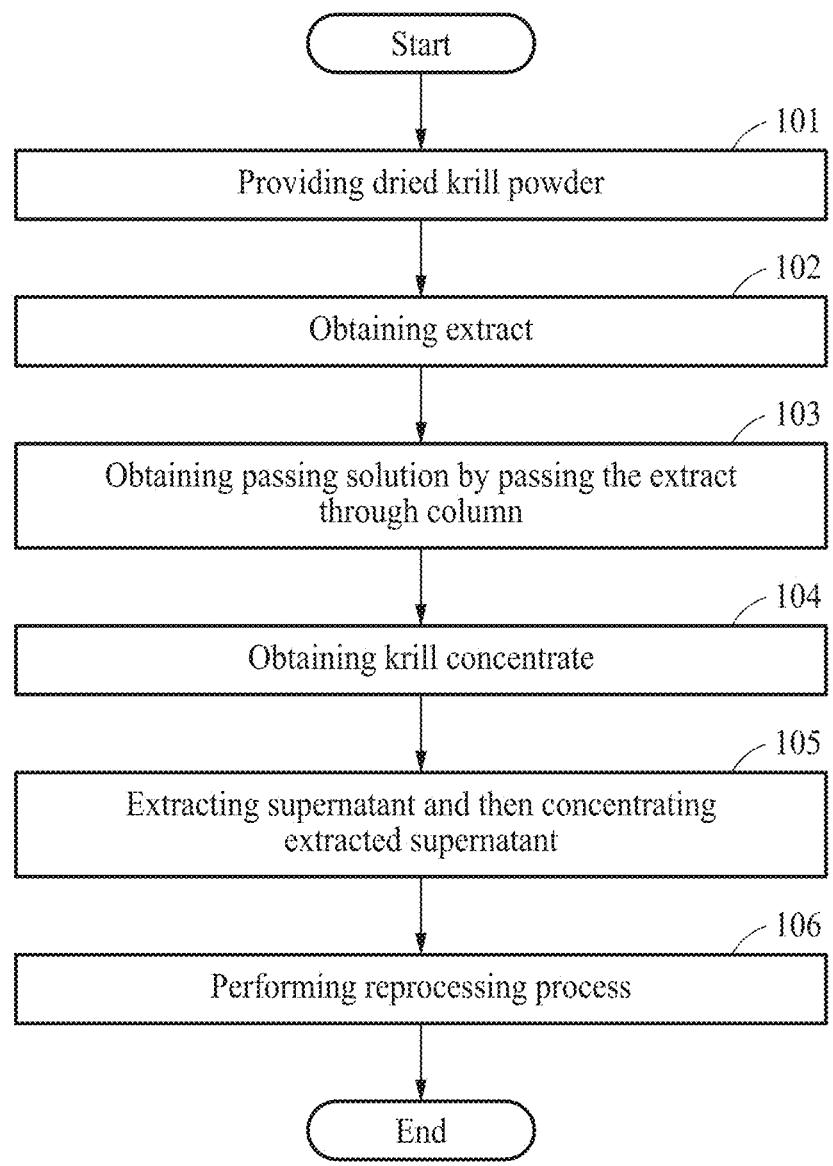

METHOD OF PREPARING KRILL OIL AND KRILL OIL COMPOSITION

CROSS-REFERENCE TO RELATED APPLICATION(S)

This application claims priority to Korean Patent Application No. 10-2020-0099434, filed Aug. 7, 2020, the entire disclosure of which is incorporated herein by reference.

BACKGROUND

1. Field of the Invention

The following example embodiments relate to a krill oil composition prepared by using krill as raw material and a preparation method thereof.

2. Description of the Related Art

Krill is a kind of plankton as a crustacean belonging to the Euphausiacea. There are about 85 species of krill around the world, and they live in the seas around the world, but the main habitat of krill is around Antarctica.

Krill is similar in small appearance to shrimp, but it is a type of animal plankton that is about 4 to 6 cm long, and krill, as food for large baleen whales, sea cats, squid, penguins, birds, seals, fish and others in the Antarctic Ocean, occupies an important part of the Antarctic ecosystem food chain.

Recently, krill has been in the spotlight for future food and resources, as krill is rich in resources, and it contains large amounts of nutrients and useful ingredients required in the human body. For example, as oil extracted from krill contains a high content of phospholipid, it is known to represent various physiological activities. Particularly, as contents of Docosahexaenoic acid (DHA) and Eicosapentaenoic acid (EPA) contained in the oil are high, the oil extracted from krill is known to have excellent efficacy in preventing cardiovascular diseases.

Meanwhile, krill oil contains a large amount of cholesterol, which causes arteriosclerosis in the blood vessels. Therefore, if a person eats foods that contain too much cholesterol, the amount of cholesterol needs to be controlled.

The foregoing background technology, which has been retained or acquired by the inventor in the process of deriving the present invention, is not necessarily a publicly-known technology which has been opened to the general public before the application for the present invention.

SUMMARY

An aspect is to provide a method of preparing krill oil with reduced cholesterol content while including rich phospholipid, and a krill oil composition prepared thereby.

Another aspect is to provide a method of preparing krill oil and a krill oil composition prepared thereby which may enhance effects as food and health functional food by securing remarkably lower cholesterol content than conventional krill oil.

According to an aspect, there is provided a method of preparing krill oil including providing a dried krill powder, obtaining an extract after adding spirits of wine to the dried krill powder; obtaining a passing solution from which salt and cholesterol are removed by passing the extract through a column, obtaining a krill concentrate by decompression-concentrating the passing solution, and obtaining krill oil by stationarily positioning a mixture obtained by adding spirits of wine to the krill concentrate, layer-separating the stationarily positioned mixture, extracting a supernatant of the layer-separated mixture, and concentrating the extracted supernatant.

In an aspect, the method may further include the step of performing a reprocessing process by dissolving the obtained krill oil in a solvent with an ethanol purity of 95% (v/v) or more to obtain a dissolved solution, and filtering and concentrating the dissolved solution.

In an aspect, the obtaining of the extract may include obtaining a spiritus extract including soluble ingredients after dissolving the dried krill powder in the spirits of wine in a temperature range of 30 to 60° C., and obtaining an extract by stationarily positioning the spiritus extract, thereby layer-separating the stationarily positioned spiritus extract in a temperature range of 10 to 25° C., and recovering an upper layer of the layer-separated spiritus extract.

In an aspect, the obtaining of the spiritus extract may include adding the spirits of wine in a volume of 500 to 800 mL per 100 g of the dried krill powder, and the spirits of wine may include ethanol with a concentration of 70 to 95% (v/v).

In an aspect, the obtaining of the passing solution may include filling at least one of zeolite and alumina ($Al_2O_3$) in the column.

In an aspect, the obtaining of the passing solution may include setting the column to a temperature range of 5 to 30° C., and setting the extract within the column to a residence time range of 0.5 to 4 hours.

In an aspect, the krill concentrate obtained by decompression-concentrating the passing solution may have a solid content of 75 to 85% (w/v).

In an aspect, the obtaining of the krill oil may include adding the spirits of wine having an ethanol concentration of 90 to 95% (v/v) in a volume ratio of 3 to 6 times the krill concentrate to the krill concentrate.

According to an aspect, there is provided a krill oil composition obtained by the method of preparing krill oil, including (a) 50 to 60% (w/w) of phospholipid, (b) 2% (w/w) or less of water, (c) 10,000 ppm or less of salt, and (d) 1.00% (w/w) or less of cholesterol.

According to an aspect, there is provided a krill oil composition including a phospholipid concentration of 50 to 60% (w/w), a water content of 2% (w/w) or less, a salt content of 10,000 ppm or less, and a cholesterol content of 1.00% (w/w) or less.

According to example embodiments, a method of preparing krill oil and a krill oil composition prepared thereby may effectively reduce the content of cholesterol while including rich phospholipid.

According to example embodiments, a method of preparing krill oil and a krill oil composition prepared thereby may enhance effects as food and health functional food by securing remarkably lower cholesterol content than conventional krill oil.

Effects of a method of preparing krill oil and a krill oil composition prepared thereby according to an example embodiment are not limited to those mentioned above, and other effects which have not been mentioned may be clearly understood by a person with ordinary skill in the art from the following description.

BRIEF DESCRIPTION OF THE DRAWING

These and/or other aspects, features, and advantages of the invention will become apparent and more readily appre- FIG. 1 is a flowchart of a method of preparing krill oil according to an example embodiment.

DETAILED DESCRIPTION

Hereinafter, example embodiments of the present invention will be described in detail with reference to the accompanying drawing. However, as the example embodiments may be subject to various changes, the scope of rights to patent applications is not restricted or limited by these example embodiments. It shall be understood that all changes, equivalents or substitutes to the example embodiments are included in the scope of rights.

Terms used in the example embodiments are used only for the purpose of explanation and should not be construed as an intention of limiting them. Expression of singular numbers includes expression of plural numbers, unless the context clearly implies otherwise. Terms such as "include", "have" and the like in the present specification designate that features, numbers, steps, actions, components, parts, or combinations thereof written on the specification exist, and it should be understood that the terms do not preclude the possibility of existence or addition of one or more other features, numbers, steps, actions, components, parts, or combinations thereof in advance.

Unless otherwise defined, all terms used here, including technical or scientific terms, have the same meanings as those generally understood by a person with ordinary skill in the art to which the example embodiments pertain. Commonly used terms such as those defined in a dictionary should be construed as having meanings consistent with the contextual meanings of related technologies, and the commonly used terms are not interpreted as ideal or excessively formal meanings unless explicitly defined in the present application.

Unless otherwise stated in the "%" used to indicate the concentration of a particular substance throughout the present specification, solid/solid is (weight/weight) %, solid/liquid is (weight/volume) %, and liquid/liquid is (volume/volume) %.

Krill is usually caught at sea and supplied by freezing or drying directly on shipboard. Krill oil may be extracted from the krill by using ethanol-containing spirits of wine as an extraction solvent. The krill oil contains various ingredients such as lipid, phospholipid, astaxanthin and cholesterol, and due to the nature of krill that lives in the sea, salt contained in seawater is also extracted along with the krill oil. A method of preparing krill oil according to an example embodiment may maximize efficacy of the krill oil by removing as much salt and cholesterol as possible from the krill oil extracted from krill.

FIG. 1 is a flowchart of a method of preparing krill oil according to an example embodiment.

Referring to FIG. 1, a method of preparing krill oil according to an example embodiment may include: a step 110 of providing a dried krill powder; a step 120 of obtaining an extract after adding spirits of wine to the dried krill powder; a step 130 of obtaining a passing solution from which salt and cholesterol are removed by passing the extract through a column; a step 140 of obtaining a krill concentrate by decompression-concentrating the passing solution; a step 150 of obtaining krill oil; and a step 160 of reprocessing the obtained krill oil.

The step 110 may include providing the dried krill powder. The step 110 includes preparing material for extracting krill oil to supply krill, in which the supplied krill is prepared in a powder state by pulverizing the supplied krill in a frozen state and performing a vacuum drying process on the pulverized krill. The vacuum drying process may be usually carried out under vacuum pressure of 20 to 100 Torr, and may be performed for 10 to 20 hours. After performing the vacuum drying process, a dried krill powder with a residual moisture content of 1 to 4% (w/w) may be provided. The step 110 may include pulverizing the obtained dried krill powder and using the pulverized dried krill powder in order to increase efficiency in the process of extracting the krill oil.

The step 120 may include obtaining an extract from the dried krill powder. The process of obtaining the extract may be carried out by the steps of obtaining a spiritus extract by adding spirits of wine to the dried krill powder, and obtaining an extract by layer-separating the spiritus extract.

A process of extracting a spiritus extract may include dipping the dried krill powder in edible ethanol-containing spirits of wine to dissolve the dried krill powder in the edible ethanol-containing spirits of wine to obtain a dissolved solution, and obtaining the spiritus extract containing soluble ingredients from the dissolved solution. In this case, the concentration of spirits of wine added to the dried krill powder is 70 to 90% (v/v), and at a temperature ranging from 30 to 60° C. as a condition for extracting the spiritus extract, three to eight times of the spirits of wine may be provided in a weight-to-volume ratio (g/ml) of the dried krill powder. For example, 500 to 800 ml of the spirits of wine may be added per 100 g of the dried krill powder.

Extraction yield of phospholipid or the like is lowered if the concentration of ethanol in the spirits of wine is 70% (v/v) or less, or extraction temperature is less than 30° C., and a problem of promoting lipid acidification may occur if the extraction temperature is 60° C. or more. Further, the extraction yield is lowered due to a solvent remaining in krill meal if three times or less of volume of the spirits of wine are provided with respect to weight of the dried krill powder, and the solvent may be wasted due to insufficient improvement in the extraction yield although additional times of the solvent are increased if times of the solvent are eight or more.

Hereafter, the step 120 may include obtaining an extract by cooling the spiritus extract, layer-separating the cooled spiritus extract, and recovering a supernatant from the layer-separated spiritus extract. The layer-separation process is performed as a red neutral fat subsides in a lower part of the spiritus extract if the spiritus extract is stationarily positioned at a temperature of 10 to 25° C. As a lower layer of the spiritus extract contains little phospholipid required by krill oil and contains a portion of cholesterol and neutral fat, the extract may be obtained by recovering a supernatant of the layer-separated spiritus extract and filtering the recovered supernatant.

Ingredients such as sodium chloride, lipid, phospholipid, astaxanthin, cholesterol and the like contained in krill meal are dissolved in the extract. If about five times the solvent are applied in the extraction process, the extract may have a solid content of 5 to 11% (w/v).

The step 130 may include obtaining a passing solution from which salt and cholesterol are partially removed from the extract by passing the extract through the column.

The column may remove salt and cholesterol from the extract that passes through the inside of the column. The inside of the column may be filled with water-absorbing fillers. For example, the inside of the column may be filled with alumina (Al$_2$O$_3$) or zeolite. Zeolite and alumina have fine pore structures, and the fine pore structures remove water from the extract by allowing water to be adsorbed in pores of the fine pore structures. It has been known that alumina may absorb water of about 5% of its own weight, and zeolite is capable of absorbing water of 30% of its own weight. Meanwhile, before passing the extract through the column, the water content of the extract may be adjusted. For example, the water content of the extract may be adjusted to 5% (v/v). Removal efficiency of the column may be reduced as the amount of water that needs to be removed through adsorption of the column increases in the column passing process if the water content of the extract is too high.

When the extract passes through the column, water in the extract may be removed by a filler filled inside the column. When water of the extract is removed, salt may be crystallized and precipitated due to a decrease in solubility. In this case, cholesterol is adsorbed on the filler in the water adsorbing and removing process so that cholesterol may be removed along with salt. Namely, the process of passing the extract through the column may perform a cholesterol-removing function along with a desalinization process.

The step 130 may include passing the extract through the column at a rate of 0.5 to 4 hours, preferably 1.5 to 2.5 hours, and more preferably about 2 hours based on a residence time of the extract inside the column. There is a drawback that the removal of salt and cholesterol is less effective when residence time of the extract inside the column is less than 0.5 hour, and the process efficiency may be rapidly decreased when the residence time of the extract inside the column is 4 hours or more. Meanwhile, the temperature of the column may be provided in a range of 5 to 30° C., preferably 10 to 25° C.

The passing solution passing through the column may have a water content of 0.3% (v/v) or less. In this case, settled salt and cholesterol may be adsorbed on the filler inside the column.

The step 140 may include obtaining a krill concentrate by decompression-concentrating the passing solution. The step 140 includes removing the solvent from the passing solution, in which the solvent is removed by concentrating the passing solution under vacuum, and a krill concentrate with a solid content of 70 to 90% (w/v), preferably 75 to 85% (w/v) may be obtained by removing the solvent from the passing solution. This is for smoothly performing the process of removing neutral lipid in the step 150.

The step 150 may include obtaining krill oil from the krill concentrate. The step 150 may include performing a layer separation process on the mixture by stationarily positioning a mixture obtained by adding ethanol-containing spirits of wine to the krill concentrate. In this case, the spirits of wine have an ethanol concentration of 90 to 95% (v/v), and ethanol may be added to the spirits of wine at a volume ratio of three to six times compared to the volume of the krill concentrate.

The mixture obtained by mixing the krill concentrate with the spirits of wine may be stationarily positioned and layer-separated at a temperature of 10 to 40° C., preferably 35° C. In this process, neutral lipid and saturated fat are separated as an infranatant, and a phospholipid-containing target extraction layer exists in an upper layer of the mixture. After removing a bottom layer of the mixture, filtering a supernatant, and vacuum-concentrating the filtered supernatant, krill oil from which salt and cholesterol are effectively removed may be obtained.

In this case, the ethanol concentration and the supply amount of the spirits of wine perform a very important function. It is difficult to effectively remove the neutral lipid and saturated fat as the amount that is layer-separated in the bottom layer becomes very small when the purity of ethanol in the spirits of wine is increased to 95% or more, and there is a problem the layer separation process is not easily carried out when the purity of ethanol is decreased to 90% or less. Further, as the amount of neutral lipid removed according to times of the spirits of wine added to the krill concentrate is determined, the more times of the solvent are increased, the greater the amount of the neutral fat is removed so that purity of phospholipid in the krill oil may be improved. It is difficult to effectively remove the neutral fat if the amount of the spirits of wine is three times or less of the krill concentrate, and a phenomenon of wasting the spirits of wine may occur as the neutral fat removing efficiency according to an increase in the amount of the spirits of wine is low if the amount of the spirits of wine is six times or more of the krill concentrate.

Krill oil obtained according to example embodiments may have a phospholipid concentration of 50 to 60% (w/w). In the step 150, the content of phospholipid in krill oil is 54 to 60% (w/w) when times of the spirits of wine are five to six times, and the content of phospholipid in krill oil is 50 to 54% (w/w) when times of the spirits of wine are three times.

The step 160 may further improve the content of phospholipid in krill oil by dissolving the obtained krill oil in a solvent, and filtering and concentrating the dissolved solution, thereby performing a reprocessing process. In the step 160, the solvent added to the krill oil may have an ethanol purity of 95% (v/v) or more, and the amount of the solvent may be three to six times of the krill oil.

It has been confirmed that the krill oil passing through the reprocessing process has a salt content range of 3,500 ppm to 10,000 ppm, preferably 4,000 ppm to 10,000 ppm. Further, the krill oil has a cholesterol content of about 1.2% (w/w) or less, preferably 1.0% (w/w) or less.

It has been confirmed that krill oil prepared through the foregoing preparation method according to example embodiments has a phospholipid content of 50 to 60% (w/w). In this case, the krill oil may have a water content of 2% (w/w) or less, and a salt content range of 3,500 ppm to 10,000 ppm, preferably 4,000 ppm to 10,000 ppm, and more preferably 4,500 ppm to 10,000 ppm. The krill oil may have a cholesterol amount range of 1.2% (w/w) or less, preferably 1.0% (w/w) or less.

Hereinafter, specific Examples will be described. However, the scope of rights to the present invention is not limited according to the following Examples.

Used Products

Used products are as follows.
(1) Column for processing: After filling a filler in a glass column having a diameter of 4 cm and a length of 15 cm, the filler filled in the glass column was used. Spherical zeolite having a diameter of 4 mm and alumina having a diameter of 3 mm manufactured by BASF Corporation were used as the filler.
(2) Analysis instrument (gas chromatography)

| Items | Conditions |
|---|---|
| Injection port temperature | 300° C. |
| Column | AT-5 |
| Column temperature | 285° C. (15 minutes) |
| Detector temperature | 300° C. |
| Carrier gas and flow rate | Nitrogen, 2.0 mL/min |
| Split ratio | 20:1 |

Experimental Method

[Cholesterol Analysis]

The analysis of cholesterol performed below is as follows.
1. A cholesterol standard undiluted solution is prepared by accurately quantifying 5 mg of cholesterol and dissolving the accurately quantified cholesterol in 5 mL of 0.5 M KOH/MeOH.
2. A standard solution is prepared by diluting the cholesterol standard undiluted solution step by step in 0.5 M KOH/MeOH.
3. Preparation of test solution
   (1) Dissolve 0.5 g of a specimen in 0.5 M KOH/MeOH.
   (2) After performing a cooling process, add 0.5 M KOH/MeOH to a volumetric flask so that a final volume becomes 10 mL.
   (3) The amount of cholesterol is analyzed through a dilution process.

[Analysis of Salt Content]

The amount of sodium ions was analyzed through ICP (Induced Combination Plasma).

Preparation Example 1

After cutting 3 kg of frozen krill, putting the cut frozen krill into a rotary concentrator, and defrosting the cut frozen krill in the rotary concentrator, the defrosted krill was vacuum-dried to 60° C. 620 g of dried krill with a water content of 1.9% (w/w) was secured by performing a drying process for about 12 hours.

After adding 500 ml of a solvent with an ethanol concentration of 95% (v/v) to 100 g of the dried krill to obtain a mixed solution, 410 ml of a spiritus extract was obtained by extracting the mixed solution at 60° C. for 1 hour to obtain an extracted solution and filtering the extracted solution. After cooling the spiritus extract to 25° C., and stationarily positioning the cooled spiritus extract for 5 hours, thereby layer-separating the cooled spiritus extract, 401 ml of an extract in an upper layer except a neutral fat layer settled and separated in a lower part of the spiritus extract was separated and obtained.

Experimental Example 1

Contents of salt and cholesterol of the extract secured in Preparation Example 1 were analyzed. It was confirmed that cholesterol in the extract had a solid content of 3.9% (w/w), and it was confirmed that salt in the extract had a solid content of 4.3% (w/w).

Preparation Example 2

A passing solution was secured by passing the extract secured in Preparation Example 1 through a column. Spherical zeolite having a diameter of 4 mm manufactured by BASF Corporation as a filler was used in the column.

401 ml of the extract was supplied at a flow rate of 1.5 ml/min so that the extract had a residence time of 2 hours in a lower part of the column. A passing solution from which salt and cholesterol had been removed while the passing solution was passing through the column via an upper part of the column was secured.

After filtering the passing solution passing through the column, the filtered passing solution was concentrated under vacuum. Hereafter, a supernatant was recovered by adding five times a solvent with an ethanol concentration of 92% (v/v) to the passing solution concentrated under vacuum to dissolve the passing solution concentrated under vacuum in the solvent, and stationarily positioning the dissolved solution at 35° C. for 6 hours, thereby removing a neutral fat separated in a lower layer of the dissolved solution. 13.9 g of krill oil with a dark wine color was obtained by vacuum-concentrating the recovered supernatant, thereby removing the solvent.

Experimental Example 2

Ingredients of the krill oil obtained in Preparation Example 2 were analyzed. It was confirmed that the krill oil obtained in Preparation Example 2 had a phospholipid content of 55.1% (w/w).

As the krill oil had a cholesterol content of 0.49% (w/w), it could be confirmed that about 87.4% of cholesterol was removed from the extract compared to Experimental Example 1, i.e., before passing the extract through the column.

As the krill oil had a salt content of 0.78% (w/w), it could be confirmed that about 81.9% of salt was removed from the extract compared to Experimental Example 1, i.e., before passing the extract through the column.

Preparation Example 3

After adding 500 ml of a solvent with an ethanol concentration of 93% (v/v) to 100 g of dried krill obtained by drying krill in Preparation Example 1, 406 ml of a spiritus extract was obtained by extracting the solvent-added dried krill at 40° C. for 1 hour to obtain an extract and then filtering the extract. After cooling the spiritus extract to 15° C., and stationarily positioning the cooled spiritus extract for 5 hours to separate and obtain 393 ml of an extract in an upper layer of the spiritus extract except a neutral fat layer settled and separated in a lower part of the spiritus extract, the extract in the upper layer was passed through a column. Spherical zeolite having a diameter of 4 mm manufactured by BASF Corporation as a filler was used in the column. In this case, a passing solution was obtained by passing the extract through the column at a flow rate of 1 ml/min such that the speed of the extract passing through the column was 3 hours based on residence time.

After filtering the passing solution passing through the column, the filtered passing solution was concentrated under vacuum. Hereafter, a supernatant was recovered by adding five times a solvent with an ethanol concentration of 90% (v/v) to the passing solution concentrated under vacuum to dissolve the passing solution concentrated under vacuum in the solvent, and stationarily positioning the dissolved solution at 25° C. for 6 hours, thereby removing a neutral fat separated in a lower layer of the dissolved solution. 12.5 g of krill oil with a dark wine color was obtained by vacuum-concentrating the recovered supernatant, thereby removing the solvent.

Experimental Example 3

Ingredients of the spiritus extract obtained in Preparation Example 3 were analyzed. Cholesterol in the spiritus extract had a solid content of 4.67% (w/w), and salt in the spiritus extract had a solid content of 4.45% (w/w).

As a result of analyzing ingredients of the finally obtained krill oil, it was confirmed that the krill oil obtained in Preparation Example 3 had a phospholipid content of 56.5% (w/w).

As the krill oil of Preparation Example 3 had a cholesterol content of 0.33% (w/w), it was confirmed that about 92.9% of cholesterol was removed from the extract compared to the spiritus extract, i.e., before passing the extract through the column. As the krill oil had a salt content of 0.88% (w/w), it was confirmed that about 80.2% of salt was removed from the extract compared to before passing the extract through the column.

Preparation Example 4

After preparing a krill extract at the same conditions as in Preparation Example 1, a passing solution was obtained by passing the krill extract through a column. Alumina having a diameter of 3 mm was used as a filler in the column. The passing solution was obtained in an upper part of the column by supplying 399 mL of an extract at a flow rate of 0.75 ml/min so that a lower part of the column has a residence time of 4 hours.

After filtering the passing solution passing through the column, the filtered passing solution was concentrated under vacuum. Hereafter, a supernatant was recovered by adding five times a solvent with an ethanol concentration of 92% (v/v) to the passing solution concentrated under vacuum to dissolve the passing solution concentrated under vacuum in the solvent, and stationarily positioning the dissolved solution at 20° C. for 6 hours, thereby removing a neutral fat separated in a lower layer of the dissolved solution. 13.0 g of krill oil with a dark wine color was obtained by vacuum-concentrating the recovered supernatant, thereby removing the solvent.

Experimental Example 4

Ingredients of the krill oil obtained in Preparation Example 4 were analyzed.

It was confirmed that the krill oil obtained in Preparation Example 4 had a phospholipid content of 54.0% (w/w).

As the krill oil of Preparation Example 4 had a cholesterol content of 0.99% (w/w), it was confirmed that about 74.6% of cholesterol was removed from the extract compared to before passing the extract through the column. As the krill oil had a salt content of 0.98% (w/w), it was confirmed that about 77.2% of salt was removed from the extract compared to before passing the extract through the column.

Although example embodiments have been described by limited drawing as described above, various modifications or changes from the aforementioned descriptions can be made by a person having ordinary skill in the art. For example, appropriate results can be achieved although described techniques are performed in order different from a described method, and/or described elements including a structure, a device and others are joined or combined in a form different from the described method, or replaced or substituted by other elements or equivalents.

What is claimed is:

1. A method for preparing krill oil comprising:
    a) mixing krill powder with 70%-95% ethanol, to extract the krill oil;
    b) passing the extract through a column comprising a stationary phase selected from the group consisting of alumina and zeolite, to remove salt and cholesterol;
    c) concentrating the column eluent;
    d) extracting the eluent with 70%-95% ethanol; and
    e) concentrate the extract.

2. The method of claim 1, further comprising mixing the concentrated extract with 95% ethanol, filtering and concentrating the solution.

3. The method of claim 1, wherein:
    a) mixing of the krill powder and 70%-95% ethanol, is carried out at a temperature of 30-60° C.;
    b) extracting the eluent with 70%-95% ethanol, is carried out at a temperature of 10-25° C.

4. The method of claim 3, wherein the 70%-95% ethanol is in a volume of 500-800 mL per 100 g of the dried krill powder.

5. The method of claim 1, wherein the column chromatography is carried out at a temperature in the range of 5-30° C., and at a time range of 0.5-4 hours.

6. The method of claim 1, wherein the eluent in step d, is extracted with 90%-95% ethanol in a volume ratio of 3-6 times the volume of the eluent.

* * * * *